United States Patent [19]

Katsuragi et al.

[11] Patent Number: 5,049,501
[45] Date of Patent: Sep. 17, 1991

[54] PRODUCTION METHOD FOR PVUI RESTRICTION ENDONUCLEASE

[75] Inventors: Nobuhiro Katsuragi; Bunsei Kawakami; Yoshihiko Maekawa, all of Tsuruga, Japan

[73] Assignee: Toyo Boseki Kabushiki Kaisha, Osaka, Japan

[21] Appl. No.: 451,201

[22] Filed: Dec. 14, 1989

[30] Foreign Application Priority Data

Dec. 19, 1988 [JP] Japan .................................. 63-321317

[51] Int. Cl.$^5$ ..................... C12N 9/22; C12N 1/21; C12N 15/55; C12N 21/00
[52] U.S. Cl. ............................. 435/199; 435/69.1; 435/252.33; 435/320.1; 935/14; 935/73
[58] Field of Search ................. 435/199, 69.1, 183, 435/320, 252.33, 172.3; 935/14, 73

[56] References Cited

FOREIGN PATENT DOCUMENTS 0193413 3/1986 European Pat. Off. .
1294824 3/1987 U.S.S.R. .............................. 435/199

OTHER PUBLICATIONS

Blumenthal, R. M. et al., 1985, "Cloning of a Restriction-Modification System from *Proteus Vulgaris* and Its Use in Analysing a Methylase-Sensitive Phenotype in *Escherichia Soli*", *Journal of Bacteriology*, vol. 164, pp. 501–509.

Wilson, G. G., 1988, "Cloned Restriction-Modification Systems-A Review", *Gene*, vol. 74, pp. 281–289.
T. R. Gingeras et al., "Two New Restriction Enconucleases from *Proteus Vulgaris*", *Nucleic Acid Research*, vol. 9 (18), 4525–4536 (1981).
K. D. Lunnen et al., "Cloning Type-II Restriction and Modification Genes", *Gene*, vol. 74, 25–32 (1988).
M. B. Mann et al., "Cloning of Restriction and Modification Genes in *E. coli*: The Hha II System from *Haemophilus haemolyticus*", *Gene*, vol. 3, 97–112 (1978).

Primary Examiner—Richard A. Schwartz
Assistant Examiner—Mary E. Mosher
Attorney, Agent, or Firm—Leydig, Voit & Mayer

[57] ABSTRACT

A recombinant vector comprising an incorporated chromosome DNA fragment containing a PvuI restriction enconuclease gene derived from *Proteus vulgaris*, a host transformed with the recombinant vector and a method of producing PvuI restriction endonuclease characterized in that the transformed host is cultivated and PvuI restriction endonuclease is harvested from the resulting culture. Since the host transformed with the recombinant vector of the present invention produces PvuI alone, it is unnecessary to remove PvuII in the purification process for PvuI, and further, since its productivity for nonspecific DNase is lower in comparison with conventional producer bacteria, DNase can be removed easily, making the production of PvuI easy.

11 Claims, 1 Drawing Sheet

PRODUCTION METHOD FOR PVUI RESTRICTION ENDONUCLEASE

BACKGROUND OF THE INVENTION

The present invention relates to a new recombinant plasmid comprising an incorporated chromosome DNA fragment containing a PvuI restriction endonuclease gene, a host transformed by introducing the plasmid and a method of producing PvuI restriction endonuclease from the host.

Restriction enzymes of Type II are enzymes with extremely high specificity which recognize and cleave a particular base sequence in deoxyribonucleic acid (DNA); with this excellent specificity, they are widely used in the field of genetic engineering.

About 100 different restriction enzymes of Type II have so far been expressed in bacteria, etc. and commercialized. Among these Type II restriction enzymes is PvuI restriction endonuclease (hereinafter abbreviated as PvuI), which recognizes and cleaves CGATCG in DNA base sequence and which is known to be produced in *Proteus vulgaris* ATCC 13315 [Nucleic Acids Research 9, 4525 (1981)].

To utilize a restriction enzyme of Type II in the field of genetic engineering, the following four requirements must be satisfied:

1) No other restriction enzyme is contained.
2) Phosphatase is not contained.
3) Nonspecific DNase is not contained.
4) Neither 3'- nor 5'-exonuclease is contained.

For this purpose, commercially available restriction enzymes are purified to high purity by using in combination nucleic acid elimination, salting-out, affinity chromatography, ion exchange chromatography, gel filtration and other means. The present inventors attempted to apply the same method as with other restriction enzymes to PvuI, and found that *Proteus vulgaris* ATCC 13315 produces PvuII restriction endonuclease which recognizes and cleaves CAGCTG, as well as PvuI, and its productivity for nonspecific DNase is higher than that of other restriction enzyme-producing bacteria, and that it is very difficult to remove these substances in the purification of PvuI.

The present inventors made intensive investigations with the aim of overcoming the two drawbacks of the above-mentioned method, namely, simultaneous production of PvuI and PvuII and high yield production of nonspecific DNase, to establish a strain which produces PvuI alone. As a result, the present inventors succeeded in obtaining a host transformed by introducing a recombinant plasmid prepared by inserting into a vector a PvuI-gene-containing chromosome DNA fragment extracted from the above-mentioned *Proteus vulgaris* ATCC 13315, and found that this host produces PvuI alone.

The present invention has been developed on the basis of this new finding.

SUMMARY OF THE INVENTION

Accordingly, the present invention comprises a recombinant plasmid comprising an incorporated chromosome DNA fragment containing a PvuI restriction endonuclease gene derived from *Proteus vulgaris*, a host transformed with the plasmid and a method of producing PvuI restriction endonuclease characterized in that the transformed host is cultivated and PvuI restriction endonuclease is harvested from the resulting culture.

Since the recombinant plasmid of the present invention and the transformed host incorporating this plasmid produce PvuI alone, it is unnecessary to remove PvuII in the purification process for PvuI and less nonspecific DNase is produced; it has thus become possible to easily produce a large amount of PvuI.

DETAILED DESCRIPTION OF THE INVENTION

Figure 1:
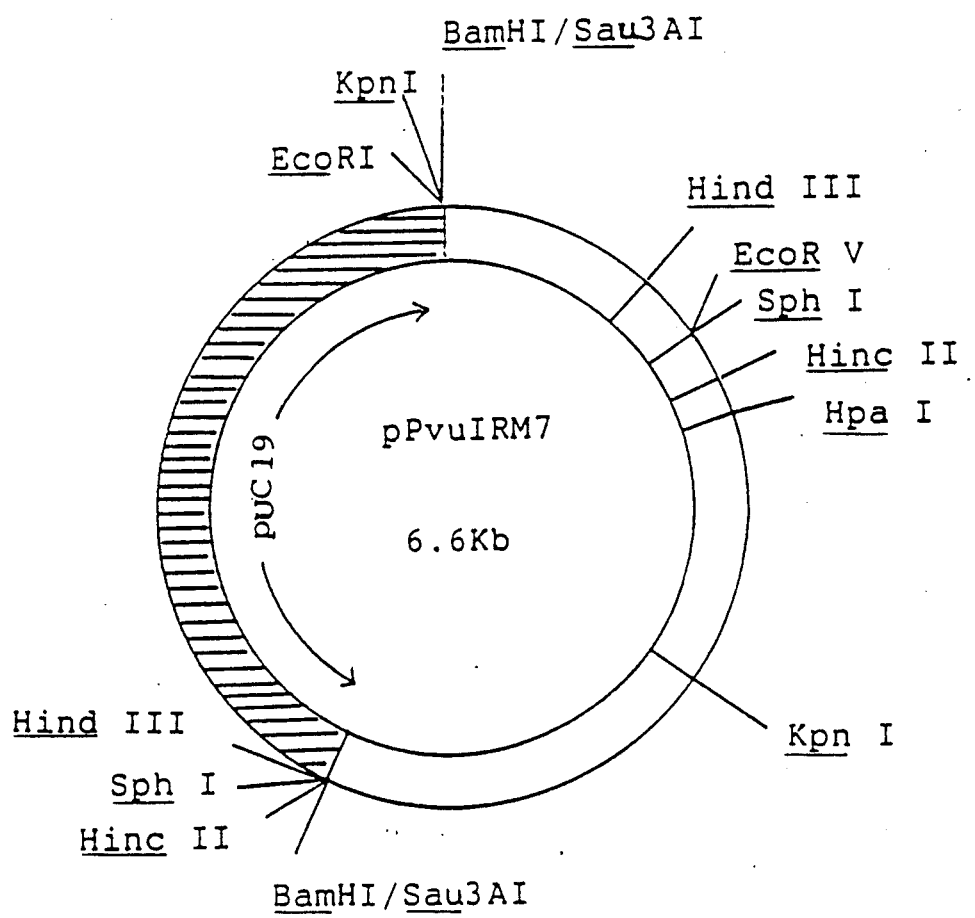
FIG. 1 shows the restriction enzyme map of the recombinant plasmid pPvuIRM7 of the present invention.

The present invention is hereinafter described in detail.

(a) Vector and its preparation

The new recombinant vector of the present invention comprises a vector capable of proliferating in cultivated cells, such as colicin E1 factor, known as an extrachromosomal DNA (plasmid) of a microorganism belonging to the genus Escherichia, and a chromosone DNA fragment containing a PvuI gene derived from *Proteus vulgaris*, such as a PvuI restriction endonuclease gene derived from *Proteus vulgaris* ATCC 13315, incorporated therein. Examples of the vector DNA include extractions from naturally occurring vectors. Also included are vector DNA species lacking a partial DNA region other than the region essential for proliferation. Examples of such vector DNA species include Col E1 strains, pMB1 strains, pSC101 strains, R6K strains and lambda phage strains.

For inserting the above-mentioned chromosome DNA fragment into the above-mentioned DNA vector, any known method can be used. For example, it is possible to use the method in which chromosome DNA is cleaved at a particular site by treatment with appropriate restriction endonuclease, then the fragment is mixed with a vector DNA treated in the same manner as above, and they are ligated using ligase.

Examples of vector DNA include pUC 19 plasmid. A new plasmid pPvuIRM7 can be obtained by inserting into this plasmid a chromosome DNA fragment prepared from *Proteus vulgaris* ATCC 13315. The restriction enzyme map of pPvuIRM7 is shown in FIG. 1. As is evident from FIG. 1, this plasmid is a circular molecule having 6.6 Kb base pairs wherein a DNA fragment containing a PvuI restriction endonuclease gene of *Proteus vulgaris* ATCC 13315 is inserted into the BamHI site among the multicloning sites of pUC 19 plasmid.

(b) Preparation of microorganism

When the ligation product of the above-mentioned chromosome DNA fragment and vector DNA thus obtained is introduced into a recipient microorganism cell by a known means of transformation, such as bacterial cell surface treatment with metal ions, a transformant strain which possesses both the desired genetic characters and the characters of the vector DNA can be obtained.

Examples of recipients which serve well for this purpose include microorganisms which are normally used in this technical field, such as *Escherichia coli* strains HB101, AG-1, SCS-1, JM109, XL-1 Blue and NM522. As a representative example thereof, mention may be made of *Escherichia coli* HB101 strain [refer to T. Maniatis et al., Molecular Cloning, A Laboratory Manual, p. 504 (1982); genetic characters F−, hsdS 20, recA13, ara-14, proA2, lacY1, galK2, rpsL 20 (Sm$^r$), xyl-5, mtl-1, sup E44, λ−)].

The microorganism obtained by transformation method by introducing the above-mentioned plasmid pPvuIRM7 into this *Escherichia coli* HB101 strain is a new microorganism, which was designated as *Escherighia coli* HB101 (pPvuIRM7) and which has been deposited since Nov. 8, 1989 under the number of FERM BP-2645 based on the Budapest Treaty on the International Recognition of the Deposit of Microorganisms, at Fermentation Research Institute, Agency of Industrial Science and Technology, the Ministry of International Trade and Industry, Japan, as transferred from the original deposit made on Nov. 29, 1988 at the same institute under the deposit number of 10420. Comparison of bacteriological nature between *Escherichia coli* HB101(pPvuIRM7) thus obtained and the DNA recipient *Escherichia coli* HB101 strain reveals are exactly identical with each other except that the former possesses capability of producing PvuI and ampicillin resistance while the latter possesses neither.

(c) Production of restriction endonuclease

For cultivating the transformant strain obtained in the process (b), it is possible to use any culture medium, as long as it is suitable for both the production of a substance produced on the basis of particular genetic information and the growth of the host microorganism. For the method of the present invention, it is acceptable to use a culture medium prepared using a basal medium, a culture medium which is normally used as growth medium for *Escherichia coli*, such as LB medium (tryptone, yeast extract, sodium chloride) or tryptone-sodium chloride medium.

It is also possible to add amino acids, vitamins and other nutrients in addition to carbon sources and nitrogen sources as needed.

Any culture method can be used, as long as the pH, temperature, oxygen supply and other conditions are suitable for the growth of microorganisms of the genus Escherichia, but it is preferable to grow the microorganism after its inoculation onto the medium until the bacterial cell quantity reaches the maximum, that is, until the logarithmic growth phase. Cultivation temperature is normally 30° to 37° C.; pH is normally between 5 and 8, preferably near 7.

The bacterial cells thus obtained are collected and then extracted via centrifugation, ultrasonic disruption and other processes, after which it is subjected to a combination of nucleic acid elimination, salting-out, affinity chromatography, ion-exchange chromatography, gel filtration and other means, whereby PvuI is obtained.

Since the plasmid of the present invention and the transformed host incorporating this plasmid produce PvuI alone, it is unnecessary to remove PvuII in the purification process for PvuI. Also, since their productivity for nonspecific DNase is lower in comparison with conventional producer bacteria, DNase can be removed easily. Therefore, it has become possible to produce PvuI with ease.

The present invention is hereinafter described in more detail by means of the following examples, but the invention is not by any means limited to them.

EXAMPLE 1

(1) Preparation of chromosome DNA containing PvuI gene

*Proteus vulgaris* ATCC 13315 was inoculated to 50 ml of L-broth medium [prepared with 10 g of polypeptone, 5 g of yeast extract and 5 g of NaCl, all per liter water, adjusted to pH 7.2], and this was followed by shaking at 37° C. Bacterial cells were collected 16 hours later. After being washed with 10 ml of TEN buffer [10 mM Tris-HCl (pH 7.6), 1 mM EDTA, 10 mM NaCl], the collected cells were suspended in 5 ml of SET buffer [20% sucrose, 50 mM Tris-HCl (pH 7.6), 50 mM EDTA]. To this suspension was added 0.5 ml of a solution [5 mg/ml TEN buffer] of lysozyme [produced by Taiyo Kagaku K.K.], and this mixture was kept standing at 37° C. for 30 minutes.

This mixture was then slowly mixed with 5 ml of TEN buffer and 5 ml of a 25% SDS solution. Then, 1 ml of a 5M NaCl solution and 10 ml of buffer-saturated phenol were added, and this was followed by 5 minutes of stirring and then 5 minutes of centrifugation at 6,500 rpm and 4° C. To the supernatant was added 10 ml of a solution of chloroform-iso-amyl alcohol [24:1], and this was followed by centrifugation for 5 minutes. Then, a two-fold amount of 95% ethanol was added to the supernatant, and the precipitated chromosome DNA was wound up while stirring the mixture with a glass rod, after which it was redissolved in 10 ml of TEN buffer. A solution (0.05 ml) of RNase [10 mg/ml 0.1M sodium acetate, 0.3 mM EDTA (pH 4.8): thermally treated at 80° C. for 10 minutes] was added thereto, and this mixture was kept standing at 37° C. for 2 hours to completely degrade the RNA. Then, 0.5 ml of a solution of pronase [2 mg/ml TEN buffer: treated at 37° C. for 15 minutes] was added, and this mixture was kept standing at 37° C. for 1 hour to completely decompose the residual protein impurity. Thereafter, 10 ml of a solution of chloroform-iso-amyl alcohol was added, and this was stirred for 5 minutes, followed by 5 minutes of centrifugation at 6,500 rpm and 4° C. A two-fold amount of 95% ethanol was added to the supernatant, and the precipitated chromosome DNA was wound up while stirring the mixture with a glass rod, after which it was redissolved in 2 ml of TEN buffer, whereby about 100 μg of chromosome DNA was obtained.

(2) Insertion of chromosome DNA fragment into vector

To 100 μg of the chromosome DNA obtained in (1) was added 0.01 unit of Sau3AI restriction endonuclease, and this was followed by reaction at 37° C. for 1 hour to partially digest the chromosome DNA. This partial digestion product was added to a solution of sucrose stratified with a density gradient of 20%, 15%, 10% and 5% in this order, and this was followed by ultracentrifugation at 23,000 rpm and 4° C. for 17 hours. The solution was fractionated on the basis of density in order to sort the chromosome DNA by size. Then, 8 units of BamHI restriction endonuclease was added to 1 μg of vector plasmid pUC 19 [produced by Toyo Boseki Kabushiki Kaisha], and this was followed by reaction at 37° C. for 1 hour to completely digest the vector plasmid. Further, 1 unit of alkaline phosphatase was added, and this was followed by reaction at 37° C. for 1 hour to remove the 5′-terminal phosphate. The chromosome DNA fragment (3 μg) corresponding to the 3-5 Kb fraction and 1 μg of the pUC 19 DNA fragment, both obtained as above, were mixed together, and this was followed by ligation reaction at 15° C. for 16 hours using 5 units of T4 phage-derived DNA ligase in the presence of 1 mM ATP and 5 mM dithiothreitol, whereby a plasmid DNA incorporating the chromosome DNA was obtained.

(3) Transformation with recombinant plasmid containing PvuI restriction endonuclease gene The *Escherichia coli* HB101 strain, the hybrid strain formed between *Escherichia coli* K-12 strain and *Escherichia coli* B strain, was inoculated to 40 ml of LB medium [prepared with 10 g of tryptone (Difco), 5 g of yeast extract and 10 g of NaCl, all per liter pure water, adjusted to pH 7.0], and this was followed by shaking culture at 37° C. until it grew up to the logarithmic growth phase. Then, cells were collected. The collected cells were suspended in a solution of CaCl$_2$ with a final concentration of 0.05M to prepare competent cells. To this cell suspension was added a solution of the plasmid DNA obtained in (2), and this was followed by reaction for 60 minutes with ice-cooling and then heat shock at 42° C. for 1 to 2 minutes to make the plasmid DNA obtained in (2) above incorporated into the cells. This cell suspension was then separately inoculated to the above-mentioned LB medium, and this was followed by shaking culture at 37° C. for 3 to 5 hours to cause transformation reaction. Then, the strain which possesses ampicillin resistance and which produces PvuI was isolated and named *Escherichia coli* HB101(pPvuIRM7) (FRI deposit number FERM BP-2645).

(4) Production of PvuI restriction endonuclease by *Escherichia coli* HB101(pPvuIRM7)

The transformant *Escherichia coli* HB101 (pPvuIRM7) (FRI deposit number FERM BP-2645) obtained in (3) was subjected to shaking culture at 37° C. for 16 hours in a 2 l flask containing 500 ml of the above-mentioned LB medium. The resulting culture was centrifuged and cells were collected. The collected cells were washed and then suspended in 25 ml of a 20 mM Tris-HCl buffer (pH 7.5) containing 10 mM MgCl$_2$ and 7 mM 2-mercaptoethanol, and this was followed by ultrasonic disruption at 0° C. for 10 minutes and then centrifugation at 12,000 rpm for 10 minutes, whereby an enzyme extract was obtained. To this enzyme extract was added ammonium sulfate powder under ice-cooling, and it was dissolved therein; the 30–80% saturated fraction (the degree of saturation is expressed by Osborne's method) was recovered by centrifugation.

This recovered precipitate was dissolved in 2 ml of a 10 mM phosphate buffer (pH 7.5) containing 2 mM 2-mercaptoethanol and 5% glycerol, and this solution was placed in a dialysis tube and dialyzed against a 100-fold amount of the same buffer overnight. Subsequently, the dialyzate was adsorbed to a column (capacity 20 ml) of phosphocellulose (produced by Whatman Co.) equilibrated with the same buffer. After column washing with a 5-fold amount of the same buffer, elution was conducted with a gradient of 0 to 1.0M KCl. PvuI restriction endonuclease was eluted near the position corresponding to a concentration of 0.5M KCl. The eluted enzyme solution was placed in a dialysis tube and dialyzed against a phosphate buffer containing 2 mM 2-mercaptoethanol and 50% glycerol to yield 0.2 ml of enzyme solution. The obtained enzyme solution was found to have an enzyme activity of 10,000 units.

The enzyme solution thus obtained contained none of other types of restriction endonuclease, phosphatase, nonspecific DNase, etc. and was thus utilizable in the field of genetic engineering. The PvuI activity was determined by dissolving 1 μg of λ-DNA in 45 μl of a reaction broth comprising 10 mM Tris-HCl buffer (pH 7.5), 7 mM magnesium chloride, 150 mM sodium chloride, 7 mM 2-mercaptoethanol and 100 μg/ml bovine serum albumin, adding 5 μl of the enzyme solution to the mixed solution, carrying out reaction at 37° C. for 1 hour, and subsequently conducting agarose gel electrophoresis. One unit of enzyme activity is defined as the enzyme activity by which 1 μg of λ-DNA is completely digested at 37° C. and pH 7.5 in 1 hour.

What is claimed is:

1. A recombinant vector which incorporates a chromosone DNA fragment containing a PvuI restriction endonuclease gene derived from *Proteus vulgaris*.

2. The recombinant vector as claimed in claim 1 wherein the vector is selected from among the group consisting of Col E1 strains, pMB1 strains, pSC101 strains, R6K strains, and lambda phage strains.

3. The recombinant vector as claimed in claim 1 wherein the recombinant vector is plasmid pPvuIRM7.

4. A host which is transformed with a recombinant vector incorporating a chromosone DNA fragment containing a PvuI restriction endonuclease gene derived from *Proteus vulgaris*.

5. The host as claimed in claim 4 wherein the vector is selected from among the group consisting of Col E1 strains, pMB1 strains, pSC101 strains, R6K strains, and lambda phage strains.

6. The host as claimed in claim 4 wherein the recombinant vector is plasmid pPvuIRM7.

7. The transformed host as claimed in claim 4 wherein the host is *Escherichia coli*.

8. A method for producing PvuI restriction endonuclease comprising culturing a host transformed with a recombinant vector incorporating a chromosone DNA fragment containing a PvuI restriction endonuclease gene derived from *Proteus vulgaris* to obtain PvuI restriction endonuclease.

9. The method for producing PvuI restriction endonuclease as claimed in claim 8 wherein the vector is selected from among the group consisting of Col E1 strains, pMB1 strains, pSC101 strains, R6K strains, and lambda phage strains.

10. The method for producing PvuI restriction endonuclease as claimed in claim 8 wherein the recombinant vector is plasmid pPvuIRM7.

11. The method for producing PvuI restriction endonuclease as claimed in claim 8 wherein the transformed host is *Escherichia coli*.

* * * * *

UNITED STATES PATENT AND TRADEMARK OFFICE
CERTIFICATE OF CORRECTION

PATENT NO. : 5,049,501
DATED : September 17, 1991
INVENTOR(S) : Katsuragi et al.

It is certified that error appears in the above-identified patent and that said Letters Patent is hereby corrected as shown below:

Column 4, line 33 delete "decompose" and substitute therefor -- degrade --.

Signed and Sealed this

Twenty-third Day of March, 1993

Attest:

STEPHEN G. KUNIN

*Attesting Officer*        *Acting Commissioner of Patents and Trademarks*